United States Patent
Beck et al.

(10) Patent No.: US 10,948,496 B2
(45) Date of Patent: Mar. 16, 2021

(54) METHOD FOR IDENTIFYING MARKER PROTEINS FOR THE DIAGNOSIS AND RISK STRATIFICATION OF BLOOD COAGULATION DISORDERS

(71) Applicant: LEIBNIZ-INSTITUT FÜR ANALYTISCHE WISSENSCHAFTEN—ISAS—E.V., Dortmund (DE)

(72) Inventors: Florian Beck, Dortmund (DE); Albert Sickmann, Dortmund (DE); Rene Zahedi, Dortmund (DE)

(73) Assignee: LEIBNIZ-INSTITUT FÜR ANALYTISCHE WISSENSCHAFTEN—ISAS—E.V., Dortmund (DE)

( * ) Notice: Subject to any disclaimer, the term of this patent is extended or adjusted under 35 U.S.C. 154(b) by 188 days.

(21) Appl. No.: 15/572,391

(22) PCT Filed: May 8, 2016

(86) PCT No.: PCT/EP2016/060245
§ 371 (c)(1),
(2) Date: Nov. 7, 2017

(87) PCT Pub. No.: WO2016/180742
PCT Pub. Date: Nov. 17, 2016

(65) Prior Publication Data
US 2018/0136221 A1    May 17, 2018

(30) Foreign Application Priority Data
May 8, 2015    (EP) ..................... 15166935

(51) Int. Cl.
*G01N 33/68* (2006.01)
*G01N 33/49* (2006.01)

(52) U.S. Cl.
CPC .... *G01N 33/6848* (2013.01); *G01N 2800/224* (2013.01); *G01N 2800/32* (2013.01); *G01N 2800/52* (2013.01)

(58) Field of Classification Search
CPC ....... G01N 2800/222; G01N 2800/224; G01N 2800/32; G01N 2800/52; G01N 33/6848;
(Continued)

(56) References Cited

U.S. PATENT DOCUMENTS

2005/0130230 A1    6/2005    Davalos et al.
2006/0172429 A1    8/2006    Nilsson et al.
(Continued)

FOREIGN PATENT DOCUMENTS

JP    2010501072 A    1/2010
JP    2014-070942 A    4/2014
(Continued)

OTHER PUBLICATIONS

Schweigel et al. Proteomics, vol. 13, 2013, pp. 1016-1027.*
(Continued)

*Primary Examiner* — Maureen Wallenhorst
(74) *Attorney, Agent, or Firm* — Troutman Pepper Hamilton Sanders LLP

(57) ABSTRACT

The invention relates to a method for identifying marker proteins for the purpose of diagnosis and risk stratification of blood coagulation disorders.

14 Claims, 4 Drawing Sheets

(58) Field of Classification Search
CPC .... G01N 33/49; G01N 33/491; Y10T 436/25; Y10T 436/25125; Y10T 436/25375
USPC ..... 436/63, 69, 86, 161, 173, 174, 175, 177; 422/73; 435/13
See application file for complete search history.

(56) References Cited

U.S. PATENT DOCUMENTS

2009/0029343 A1* 1/2009 Larsen ................ C07K 14/473 435/4
2010/0304406 A1 12/2010 Guo et al.

FOREIGN PATENT DOCUMENTS

| WO | 2001/096594 A2 | 12/2001 |
|---|---|---|
| WO | 2008020013 A2 | 2/2008 |
| WO | 2008/131261 A2 | 10/2008 |
| WO | 2010060918 A1 | 6/2010 |
| WO | 2011/042467 A1 | 4/2011 |

OTHER PUBLICATIONS

Beck et al. Blood, vol. 129, No. 2, Jan. 12, 2017, pp. e1-e12.*
Beck, F. et al., "Time-resolved characterization of cAMP/PKA-dependent signaling reveals that platelet inhibition is a concerted process involving multiple signaling pathways" e-Blood, vol. 123, No. 5, Jan. 30, 2014, pp. e1-e9.
Lewandrowski, U. et al., "Platelet membrane proteomics: a novel repository for functional research", e-Blood, vol. 114, No. 1, Jul. 2, 2009, pp. e10-e19.
Translation of the International Search Report for PCT/EP2016/060245 dated Jun. 7, 2016, 3 pages.
International Preliminary Report on Patentability issued in International Application No. PCT/EP2016/060245 dated May 4, 2017.
Schweigel, Hardy et. al., "Deciphering of ADP-induced, phosphotyrosine-dependent signaling networks in human platelets by Src-homology 2, region (SH2)-profiling", Proteomics 2013, vol. 13, pp. 1016-1027. DOI: 10.1002/pmic.201200363.
Satoh et al., "Platelet aggregometry in the presence of PGE1 provides a reliable method for cilostazol monitoring", vol. 130, pp. 616-621 (2012).

* cited by examiner

METHOD FOR IDENTIFYING MARKER PROTEINS FOR THE DIAGNOSIS AND RISK STRATIFICATION OF BLOOD COAGULATION DISORDERS

CROSS-REFERENCE TO RELATED APPLICATIONS

This application is a U.S. national phase application under 35 U.S.C. § 371 of International Patent Application No. PCT/EP2016/060245, filed on May 8, 2016, and claims the benefit of priority of the prior European Patent Application No. 15166935.5, filed on May 8, 2015, with the entire contents of both applications incorporated herein by reference.

FIELD OF TECHNOLOGY

The invention relates to a method for identifying marker proteins for the purpose of diagnosis and risk stratification of blood coagulation disorders.

BACKGROUND

For the purpose of providing a suitable therapy, it is necessary to make an early diagnosis of, and differentiation between blood coagulation disorders in conjunction with the need to make clinical decisions, in particular in emergency medicine.

Due to the action of various substances (collagen, thrombin, immune complexes, among others), thrombocytes secrete platelet factors stored in granules (degranulation), which above all activate the blood coagulation system or haemostasis inherent to the body, thus forming a thrombus. However, the activation of the thrombocytes can become disrupted, in particular for genetic or pathological reasons. This is usually associated with an increased risk of serious cardiovascular or secondary effects. It is therefore necessary to determine the degree of activation and activation ability (AaA) of thrombocytes. This is linked to the degree of phosphorylation of proteins in thrombocytes, such as VASP, and is subject to a kinase activity.

The individual determination of the AaA of thrombocytes is intended to contribute to the ability to provide a more accurate classification of patients into risk groups and a suitable personalised therapy (preparation, dosing, duration, combination), and to additionally control this therapy.

In the prior art, the AaA of thrombocytes are analysed in numerous thrombocyte function tests, wherein thrombocytes are activated with agonists or via shear forces, and for example the aggregation is determined so as to determine the activation ability (response) of thrombocytes, for example after treatment with drugs, such as copidogrel.

These function tests comprise three main types in particular: (i) aggregation-based tests, such as LTA (light transmission aggregometry), (ii) shear force-dependent tests, and (iii) throughflow cytometry. Generally, it has been found that, on account of the large number of different methods and the low standardisation of the tests (and pre-analytics), the correlation between various tests is low on the one hand, and on the other hand the validity of the individual tests with regard to predicting the drug response and therapy management is unsatisfactory in practice (Krisha et al., Circulation 2012, 1288-1303). Therapy management by means of gene typing is also discussed—and therefore both methods are currently viewed critically (Krisha et al., Circulation 2012, 1288-1303). The VASP assay (testing system for detecting the activity of cyclo-nucleotide-dependent protein kinases, DE 100 29 210 A1), which determines the degree of phosphorylation of the VASP protein via phosphospecific antibodies, is currently one of the gold standards for checking the thrombocyte function status/activation status from small amounts of blood.

It would appear that the measurement of an individual kinase substrate or parameter, as used in most tests, is not sufficient to determine the AaA of thrombocytes—particularly in the context of different activation and inhibition signal pathways which are known in thrombocytes.

A disadvantage of the known diagnosis methods is therefore that an early and complete detection of patients at risk is inadequate, and therefore a risk stratification and therapy management are inadequate. One object underlying the invention therefore lies in developing the risk stratification of blood coagulation disorders so as to enable an improved detection of patients at risk, with a further object being that of identifying corresponding marker proteins.

It is also disadvantageous that in the prior art only insufficient sensitivity and/or specificity of the marker proteins is usually achieved.

DETAILED DESCRIPTION

Figure 1:
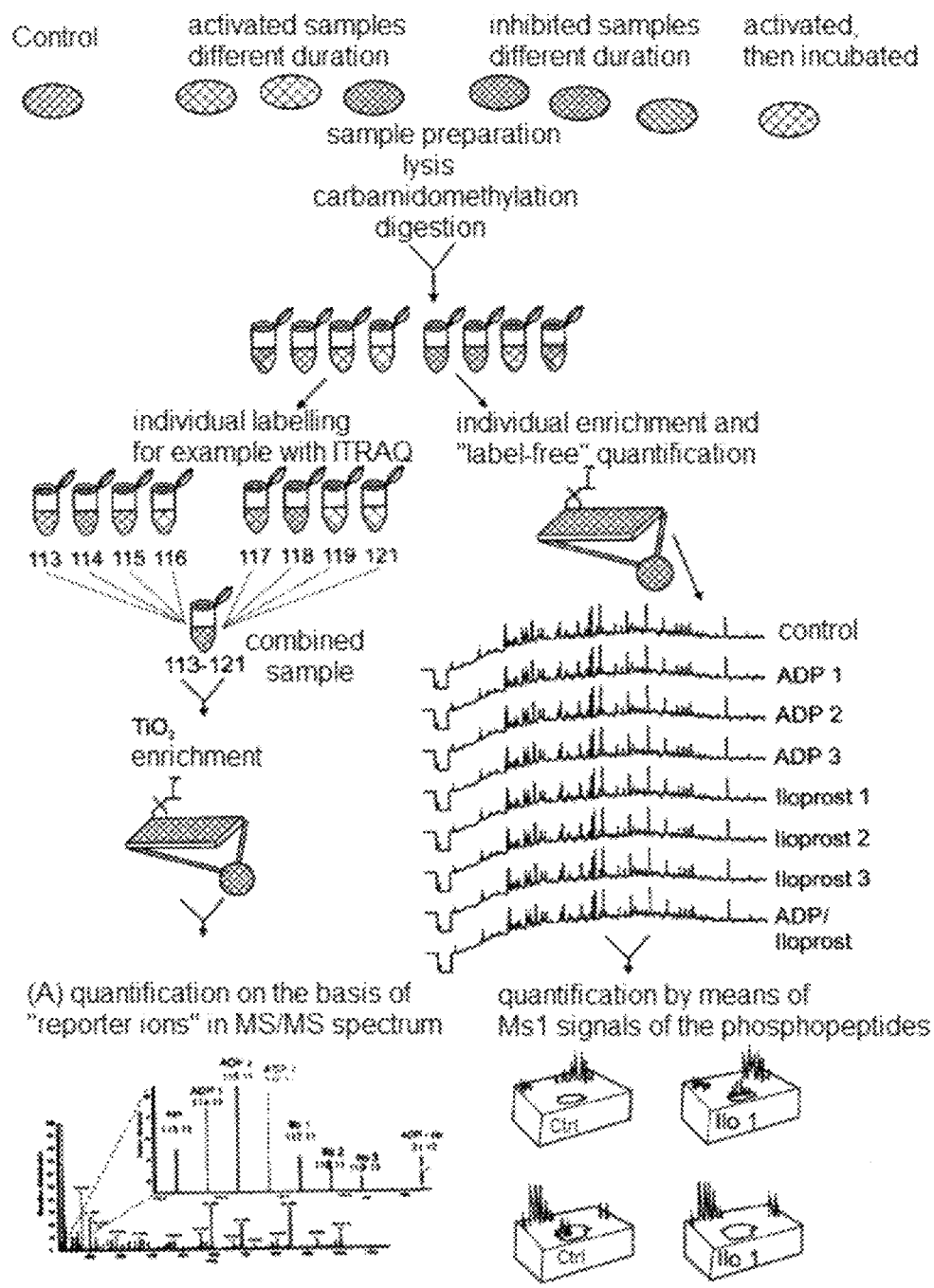
FIG. 1 depicts an experimental sequence after isolation and stimulation (activation) of the thrombocytes.

The object of the present invention is therefore to provide a method for identifying marker proteins for the purpose of diagnosis and risk stratification of blood coagulation disorders, and also a method for determining the degree of activation and activation ability of thrombocytes, said method being performed on the blood of a patient (test subject).

The object is achieved by a method according to claim 1, comprising the following steps:

i.) providing blood, whole blood, blood serum or blood plasma containing thrombocytes, ii.) aliquoting into at least two aliquots, iii.) A. adding a thrombocyte activator to at least a first aliquot and B. adding a thrombocyte inhibitor to at least a second aliquot, and repeating the addition once or more, and optionally C. adding a thrombocyte activator and adding a thrombocyte inhibitor to at least a third aliquot or vice versa, and optionally repeating the respective additions once or more, iv.) lysing the cells, in particular thrombocytes from iii.) A. B. and C. in the particular aliquot, v.) extracting the proteins and digesting them to form peptides by means of proteases, vi.) enriching and separating the phosphorylated peptides, vii.) performing an analysis by means of quantitative mass spectrometry, and evaluation, wherein phosphorylated peptides are selected which at the same time demonstrate an increased or reduced phosphorylation from iii.) A over time and which demonstrate, oppositely, reduced or increased phosphorylation from iii. B) over time and which optionally demonstrate a reduced or increased phosphorylation in comparison with phosphorylated peptides from iii.) C.

(hereinafter: method according to the invention)

Steps iii.) to vii.) can be repeated individually or jointly as often as desired. The additions in iii.) C. can be performed at 30-second intervals. Furthermore, the steps can all be automated or can be automated individually.

For diagnosis or risk stratification, it is merely necessary that one or more marker proteins are identified which demonstrate a different, more specifically opposite phosphorylation to one another according to iii.) A and iii.) B, more specifically either an increased (reduced) phosphorylation in iii.) A (presence of a thrombocyte activator) and reduced (increased) phosphorylation in iii.) B (presence of a thrombocyte inhibitor), or vice versa (indicated between parentheses in italics). In any sample, approximately 1% of the total proteins demonstrate this behaviour in accordance with the invention.

Step i.): Blood is preferably taken in the form of fresh blood from a patient or test subject, for example during the course of a blood sampling process (finger prick).

Step ii.): The aliquoting (dividing of the sample) can be performed so as to produce an arbitrary number of aliquots (tubes) (for example 360 or more).

In step iii.) suitable thrombocyte activators, such as ADP, collagen, thrombin, immune complexes, thrombocyte aggregation inhibitors, inter alia, are clopidogrel, prasugrel or acetylsalicylic acid.

In step iii.) suitable thrombocyte inhibitors are those such as iloprost (prostacyclin analogue) and NO (nitrogen monoxide) donors, such as molsidomine or nitroprusside.

The third aliquot iii.) C. serves to further validate the results and can be consulted optionally. A blind sample D. (aliquot from ii.)) can optionally also be retained as control by making no addition of thrombocyte activators or thrombocyte inhibitors in step iii.), but performing steps iv.) to vii.).

In step iv). the lysis can be performed using any methods, in particular preferably with a lysis buffer (2% SDS inclusive of phosphatase inhibitors), with exact composition according to Beck et al., Blood 2014, 123(5):e1-e10. The lysis stops the cellular signal response or "freezes" the thrombocyte activity.

In step v.) the extraction can be performed by any methods, in particular preferably with the aid of an ethanol precipitation or filter-aided sample preparation (Wisniewski et al., Nat Meth, 6 (2009) 359-362)). A proteolytic digestion can be performed for example by means of trypsin (Dickhut et al., J Proteome Res 2014, 6; 13(6):2761-70), whereby peptides with an average length of 14 amino acids are obtained, which can be easily detected and quantified using mass spectrometry (preferred range between 7 and 35 amino acids).

In order to enrich the obtained peptides for the purpose of quantitative mass spectrometry in step vi.), the peptides can be used labelled or label-free. A suitable label, in particular isotope label, can be provided for example by means of iTRAQ (Ross et al., Mol Cell Proteomics. 2004; 3:1154-1169), ICPL (Kellermann J et al., Methods Mol Biol. 2012; 893:143-53) or dimethyl labelling (Hsu et al., Anal Chem. 2003; 75:6843-6852)). Of course, the aliquots can also be quantified individually. The phosphorylated peptides, which are labelled or unlabelled, are separated by means of titanium dioxide (Dickhut et al., Methods Mol Biol. 2014; 1156:417-30)—alternatively, other methods of phosphopeptide enrichment can also be used, such as ERLIC (Loroch et al, Anal Chem, 2015, 3; 87(3):1596-604) or Ti4+-IMAC (De Graaf, Mol Cell Proteomics. 2014; 13(9):2426-34).

The phosphorylated peptides separated in this way are fed to a quantitative mass spectrometry, preferably by means of LC-MS/MS.

Within the scope of this invention, the term "quantitative mass spectrometry" is understood to mean one in which "MS/MS" (also: tandem mass spectrometry) is used. Here, MS1 scans are firstly acquired in the mass spectrometer, which record the mass/charge ratios (m/z) of the peptide ions present, and then these peptide ions are fragmented by energy transfer, for example by collision with inert gas molecules (N2 or Ar). The ions then disintegrate very specifically to form other (lighter) ions, which are read in the MS/MS scan. Many combinations of the analysers can be used, such as triplequads (QqQ), QqTOF (quadruple-quadruple-TOF), TOF-TOF and TRAP-Orbitrap and further hybrid mass spectrometers.

Besides conventional MS/MS and $MS^3$ (Ting et al, Nat Meth, 8(11), 937-940 (2011), MRM (Multiple Reaction Monitoring) and PRM (Parallel Reaction Monitoring) can also be used. Furthermore, coupling with liquid chromatography is preferred in accordance with the invention, in particular in the form of LC-MS/MS. In particular, LC-MS/MS allows a time-resolved quantitative mass spectrometry of the phosphorylated peptides from step vi.)

Due to the large data volumes (10,000e spectra, 1000e quantified phosphorylated peptides) the evaluation must be performed bioinformatically. To this end, the data is evaluated on the one hand qualitatively so as to identify the detected peptide sequences (i.e. determine amino acid sequence and assign origin protein, localise phosphorylation point within the sequence), and on the other hand quantitatively (reading of the signal intensities in the mass spectrometer as a measure for the amount of peptide). The identification occurs with the aid of search algorithms such as Mascot (Perkins D N et al., Electrophoresis. 1999; 20:3551), and the localisation of the phosphorylation point is performed with algorithms such as phosphoRS (Taus et al., J Proteome Res. 2011; 10(12):5354-62.) Here, the information from the MS and MS/MS scans is compared with the sequence information from protein sequence databases (for example obtainable from www.uniprot.org). The quantification is dependent on the method ultimately used. In the case of reporter-ion-dependent methods (iTRAQ, TMT) the reporter signals generated on the basis of the labels are used in the MS/MS spectrum as a measure for the relative amounts of the peptide in the different samples (FIG. 1). In the case of non-isobaric labelling methods (ICPL, dimethyl) and label-free quantification, the quantitative information is read at MS scan level (FIG. 1). The signals are converted bioinformatically into intensity values (for example with the aid of Proteome Discoverer software from Thermo Scientific), and changes between the samples can thus be quantified.

The term according to the invention "blood coagulation disorders" comprises all procedures and processes which in particular are based on impaired haemostasis and lead to a reduced or increased blood coagulation. In particular, in the case of surgical interventions, such blood coagulation disorders can lead to life-threatening complications. "Blood coagulation disorders" in accordance with the invention comprises diseases and states and also related diseases, such as thrombosis, stroke, heart attack, circulatory disorders and cardiovascular diseases.

All mentioned indications are additionally described in Pschyrembel, De Gruyter, 266$^{th}$ edition, Berlin 2015.

The term "risk stratification" in accordance with the invention comprises the discovery of patients, in particular emergency patients and patients at risk, who have a poorer prognosis for the purpose of more intense diagnostics and therapy/treatment of blood coagulation disorders and associated diseases and related diseases, in particular thrombosis, stroke, heart attack, circulatory disorders and cardiovascular diseases, with the objective of enabling the most favourable course possible of these illnesses. A risk stratification according to the invention consequently allows an effective treatment method, which for example can lead to a targeted therapy management.

The invention therefore also relates to the identification of patients with increased risk and/or an unfavourable prognosis of blood coagulation disorders, more specifically in symptomatic and/or asymptomatic patients, in particular emergency patients.

In particular in cases of emergency and/or intensive-care medicine, a reliable stratification can be provided particularly advantageous by means of the method according to the invention. The method according to the invention therefore enables clinical decisions which lead to a rapid success of the therapy and to an avoidance of death. Such clinical decisions also comprise further treatment by means of medicinal products for the treatment or therapy of blood coagulation disorders, in particular of thrombocyte aggregation inhibitors (TAIs), such as abciximab, acetylsalicylic acid, a combination of acetylsalicylic acid and dipyridamol, clopidogrel, eptifibatid, ilomedin, prasugrel, ticagrelor, ticlopidin, tirofiban.

The invention therefore also relates to a method for the diagnosis and/or risk stratification of patients by blood coagulation disorders in order to make clinical decisions, such as further treatment and therapy by means of medicinal products, preferably in time-critical intensive-care medicine or emergency medicine, including decisions to hospitalise patients.

In a further preferred embodiment, the method according to the invention therefore relates to therapy management of blood coagulation disorders.

In a further preferred embodiment of the method according to the invention, this method is used for diagnosis and/or risk stratification for prognosis, differential diagnostic early detection and identification, severity assessment and prognostic assessment in conjunction with therapy.

In a further preferred embodiment the invention relates to a method for in vitro diagnostics for early diagnosis or differential diagnosis or prognosis of blood coagulation disorders in a patient to be examined.

In one embodiment of the method according to the invention blood is taken from the patient to be examined, optionally whole blood or serum or obtainable plasma, and the diagnosis is performed in vitro/ex vivo, i.e. outside the human or animal body.

Due to the determination of the phosphorylated peptides by the method according to the invention, a high sensitivity and specificity are attained (see the examples and the drawings) and the diagnosis or risk stratification can be performed on the basis of the amount present of corresponding phosphorylated proteins in at least one patient sample by the method according to the invention.

EXAMPLES AND DRAWINGS

The following examples and drawings serve to explain the invention, without limiting it.

Once fresh blood has been taken, thrombocytes are first isolated by means of differential centrifugation (Beck et al., Blood 2014, 123(5):e1-e10). The sample is then divided into aliquots, of which (i) one serves as an untreated control, whereas (ii-iv) three are stimulated with an activating agonist, such as ADP or thrombin for 10 s, 30 s and 60 s, and (v-vii) three are inhibited, for example by adding iloprost or diethylamine nonoate, also for 10 s, 30 s and 60 s, and (viii) one sample is activated for 30 s and is then inhibited for 30 s.

For the systematic search for suitable marker proteins, different concentrations, activators/inhibitors and times should be selected. Each sample is quickly directly lysed by means of a lysis buffer (for example 2% SDS, phosphatase inhibitor cocktail) following the stimulation. Once the lysis has been performed the proteins are extracted by means of ethanol precipitation or filter-aided sample preparation (Wisniewski et al., Nat Meth, 6 (2009) 359-362). Proteolytic digestion by means of trypsin is then performed (Dickhut et al., J Proteome Res 2014, 6; 13(6):2761-70).

The generated peptide samples are then either chemically labelled by means of stable isotope labelling (for example iTRAQ Label by AB Sciex) and then combined, or are treated and analysed individually for what is known as a label-free analysis. In order to separate phosphorylated peptides important for the analysis from the large excess of non-phosphorylated peptides and make them accessible for mass spectrometry, phosphorylated peptides are enriched by means of titanium dioxide (Dickhut et al., Methods Mol Biol. 2014; 1156:417-30).

The phosphopeptide samples are then either analysed individually (label-free analysis) or the combined sample (iTRAQ) is analysed by means of nano-LC-MS/MS (see FIG. 1).

FIG. 1: Experimental sequence after isolation and stimulation (activation) of the thrombocytes.

The phosphorylated peptides and consequently the signal response of the thrombocytes to the activation or inhibition will become clear ultimately in the quantification (bottom left: quantification by means of reporter ions from the chemical labels; bottom right: "label-free" quantification on the basis of the signal intensity of the phosphopeptide in the respective samples). (A) Exemplary example of a potential new marker protein. The rise in the signals ADP 1, ADP2 and ADP3 compared to the control shows an increase of the phosphorylation after ADP stimulation, whereas the signals Ilo 1, Ilo 2, Ilo 3 indicate a reduction of the phosphorylation after inhibition. The increase by ADP stimulation can be compensated for ultimately by addition of iloprost (ADP/Ilo). In principle, it is also possible, by contrast, that ADP leads to a reduction and iloprost leads to an increase.

FIG. 2: Explanation of the method according to the invention.

Figure 2A:
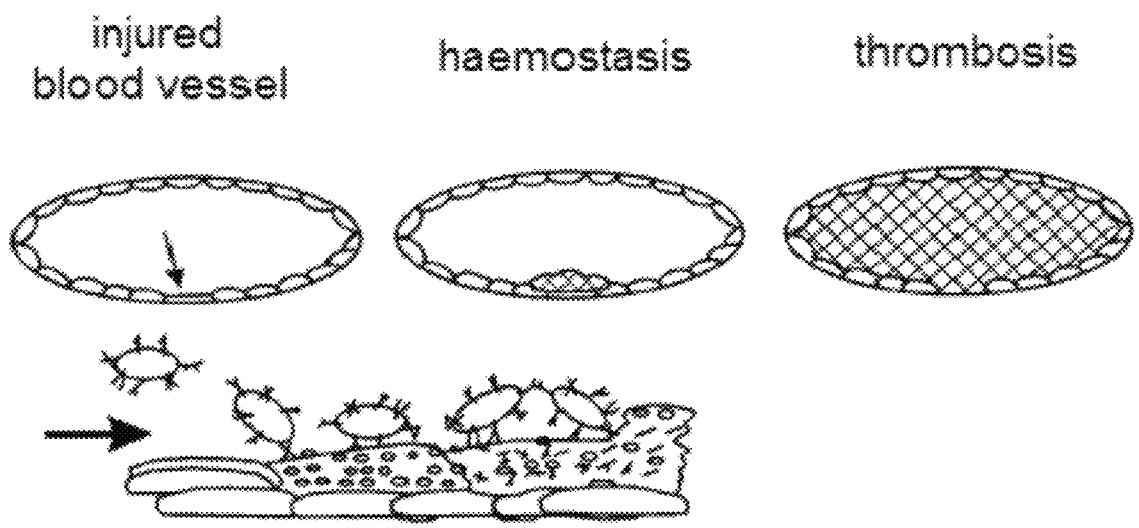
FIG. 2A illustrates how thrombocytes assume a key role in the physiological process of haemostasis.

FIG. 2A: Thrombocytes assume a key role in the physiological process of haemostasis. In other words, if a blood vessel is injured, thrombocytes recognise this, are thus "activated" and aggregate, and thus form a stable thrombus, which closes the wound, thus stops the blood loss, and also prevents the infiltration of pathogens and foreign substances. This process is performed within a few seconds to minutes. In the blood flow, compounds acting in an inhibitory manner are present inter alia, which are intended to prevent this thrombocyte activation from occurring spontaneously. If this sensitive system is destroyed, it can result in thrombosis, which close blood vessels so that the blood supply to the tissue is interrupted and ultimately could lead to an infarction.

Figure 2B:
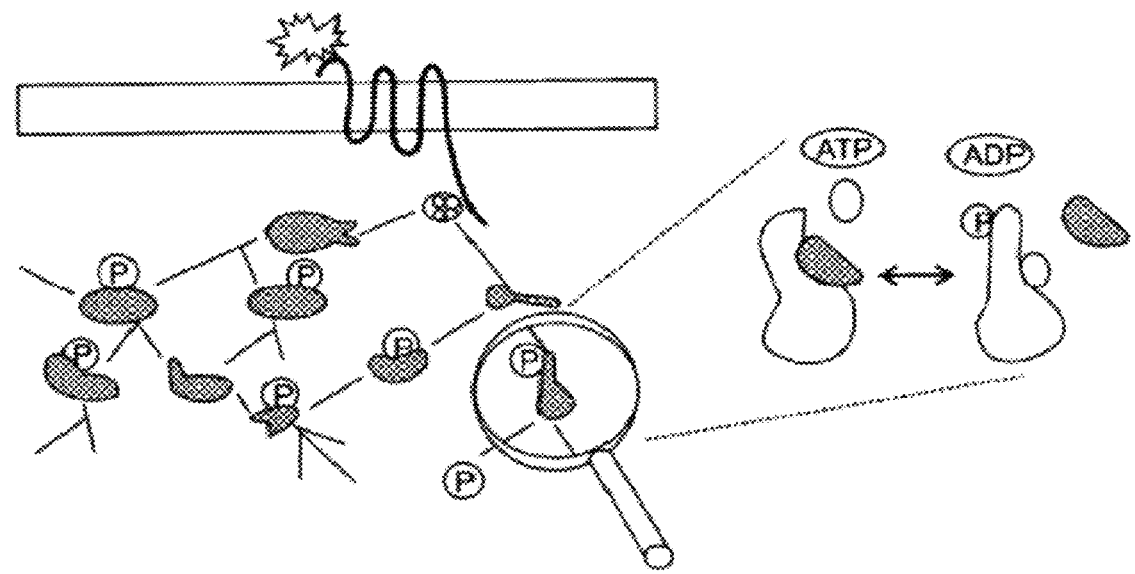
FIG. 2B illustrates how the activation of thrombocytes occurs via what are known as phosphorylation cascades.

FIG. 2B: The activation of thrombocytes occurs via what are known as phosphorylation cascades. Activating or inhibiting components from the blood system bind to membrane receptors and thus trigger a "downstream signalling". In other words, enzymes selectively bind phosphate residues via covalent bonds to proteins (kinases) or remove them (phosphatases). The phosphate groups lead to a charge change at the surface of proteins and thus to a change of their three-dimensional structure. The latter in turn defines (a) which proteins interact with one another, and (b) which function and (c) activity the protein ultimately has. The phosphorylation is thus a reversible and finely adjusted system for rapid regulation of cellular processes.

Figure 2C:
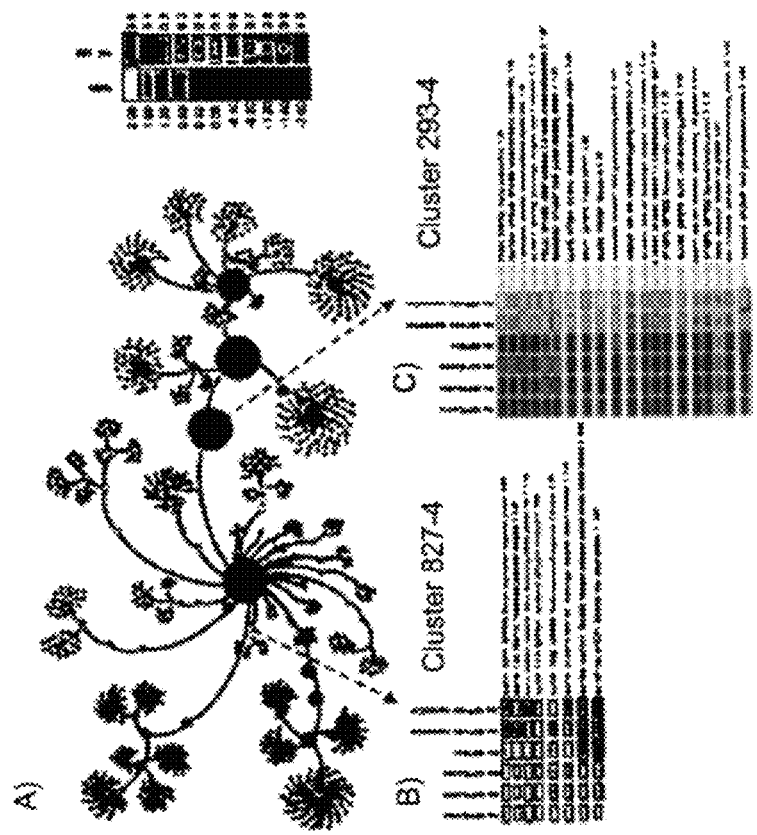
FIG. 2C illustrates that by means of quantitative mass spectrometry (MS), changes to the protein phosphorylation of hundreds to thousands of proteins can now be measured.

FIG. 2C: By means of quantitative mass spectrometry (MS), changes to the protein phosphorylation of hundreds to thousands of proteins can now be measured. To this end, thrombocytes from healthy donors are isolated preferably from fresh blood, and the approximately 4000-5000 proteins present are purified and proteolytically cleaved into smaller fragments, or what are known as peptides. These peptides are subjected to an enrichment so that only those that contain one or more phosphate residues are fed to the analysis. Lastly, the quantitative MS is used to detect differences in the phosphorylation after stimulation of thrombocytes by activating (ADP) or inhibiting (iloprost) compounds. The time-resolved quantitative data are evaluated bioinformatically so as to gain information about the "network" (totality of signal pathways).

Figure 2D:
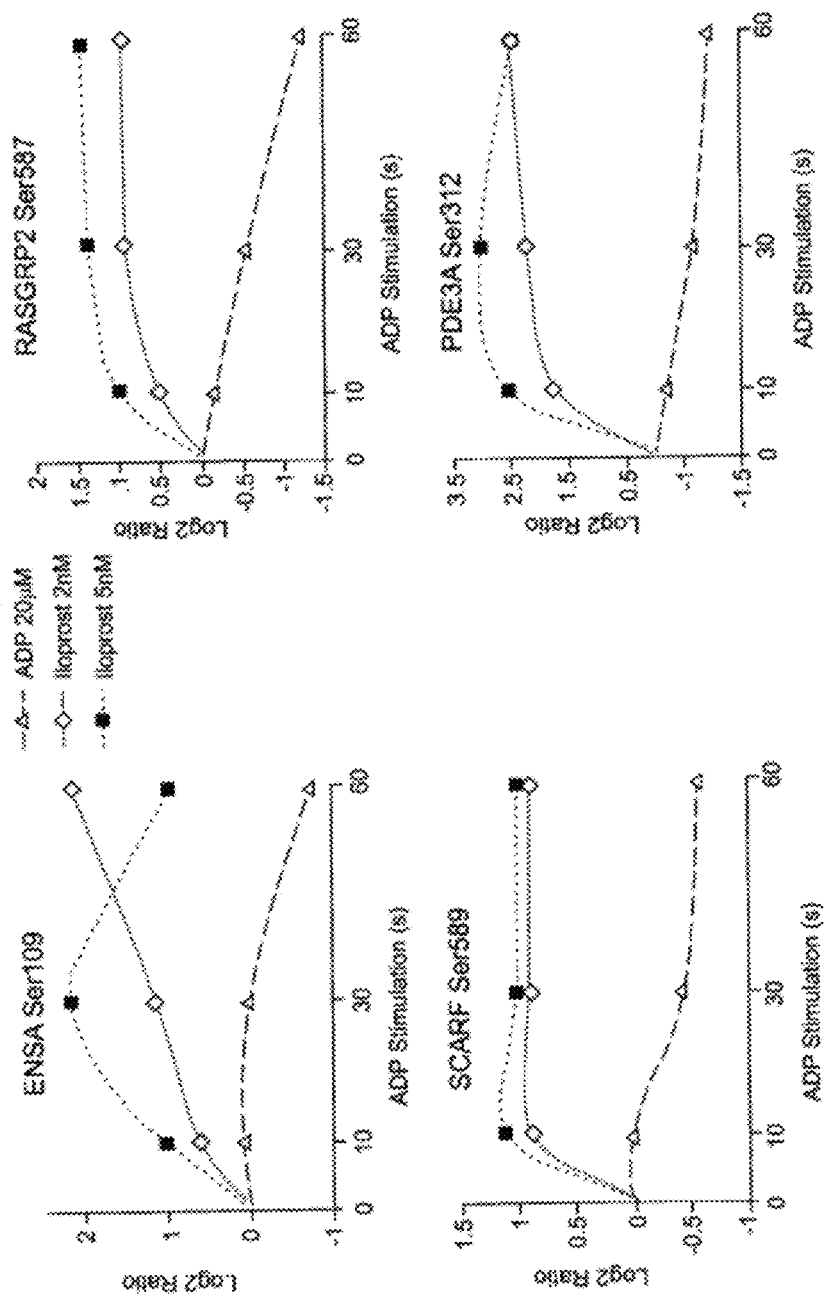
FIG. 2D illustrates how time-resolved quantitative mass spectrometry data are used to detect significantly different (i.e. opposite) progressions of phosphorylation at certain proteins.

FIG. 2D: The time-resolved quantitative mass spectrometry data are used to detect significantly different (i.e. opposite) progressions of phosphorylation at certain proteins. Although the exact function of a certain phosphorylation point on a protein is not known, opposite progressions indicate a central role in the equilibrium (homeostasis) of the thrombocytes. A phosphorylation point which increases with activation and decreases with inhibition, and vice versa, indicates a central role in both processes—and thus represents a potential candidate (target) for diagnostic and therapeutic purposes and can be used for risk stratification of blood coagulation disorders and for determination of the degree of activation and activation ability of thrombocytes.

The invention claimed is:

1. A method for identifying marker proteins for diagnosis and risk stratification of blood coagulation disorders, comprising the following steps:
    (i) providing a sample comprising whole blood, blood serum, or blood plasma containing thrombocytes,
    (ii) aliquoting the sample into at least two aliquots,
    (iii)(A) adding a thrombocyte activator to at least a first aliquot and
    (B) adding a thrombocyte inhibitor to at least a second aliquot, and repeating the addition once or more, and optionally
    (C) adding a thrombocyte activator and a thrombocyte inhibitor to at least a third aliquot, and optionally repeating the respective additions once or more,
    (iv) lysing cells in each of the first aliquot, the second aliquot, and optionally the third aliquot,
    (v) extracting proteins from each of the first aliquot, the second aliquot and optionally the third aliquot, and digesting the extracted proteins to form peptides by means of proteases,
    (vi) enriching and separating phosphorylated peptides from the peptides formed by digestion,
    (vii) performing an analysis of the phosphorylated peptides by means of quantitative mass spectrometry, and identifying phosphorylated peptides which at the same time demonstrate an increased or reduced phosphorylation from (iii)(A) over time and which demonstrate, oppositely, reduced or increased phosphorylation from (iii)(B) over time and which optionally demonstrate a reduced or increased phosphorylation in comparison with phosphorylated peptides from (iii)(C), wherein the identified phosphorylated peptides can serve as marker proteins for the diagnosis and the risk stratification of blood coagulation disorders.

2. A method for determining a degree of activation and activation ability of thrombocytes, wherein the method according to claim 1 is performed on a patient's blood, wherein a presence of an identified phosphorylated peptide indicates the degree of activation and activation ability of the thrombocytes in the blood of the patient.

3. A method for identification, diagnosis and risk stratification of a patient at increased risk of and/or having an unfavourable prognosis of blood coagulation disorders and blood diseases, comprising undertaking the method according to claim 1.

4. The method according to claim 3, wherein the patient is a symptomatic or asymptomatic patient.

5. The method according to claim 4, wherein the patient is an emergency patient.

6. The method according to claim 3, wherein the blood diseases are thrombosis, stroke, heart attack, a circulatory disorder or a cardiovascular disease.

7. A method for identification, diagnosis and risk stratification for therapy management of blood coagulation disorders and blood diseases in intensive-care medicine or emergency medicine, comprising undertaking the method according to claim 1.

8. The method according to claim 7, wherein the blood diseases are thrombosis, stroke, heart attack, a circulatory disorder or a cardiovascular disease.

9. A method for making clinical decisions with regard to further treatments and therapies by means of medicinal products, comprising undertaking the method according to claim 1.

10. The method according to claim 9, wherein the method is undertaken in intensive-care medicine or emergency medicine.

11. The method according to claim 9, wherein the clinical decision is a decision with regard to hospitalization of a patient.

12. The method according to claim 1, wherein the method is suitable for prognosis, differential diagnostic early detection and identification, severity assessment and prognostic assessment in conjunction with therapy.

13. The method according to claim 1, wherein phosphorylated peptides are identified that at the same time demonstrate an increased phosphorylation from (iii)(A) over time and which demonstrate a reduced phosphorylation from (iii)(B) over time.

14. The method according to claim 1, wherein phosphorylated peptides are identified that at the same time demonstrate a reduced phosphorylation from (iii)(A) over time and which demonstrate an increased phosphorylation from (iii)(B) over time.

* * * * *